United States Patent [19]

Chao

[11] Patent Number: 4,845,295

[45] Date of Patent: Jul. 4, 1989

[54] ALKYLATION OF AMINE COMPOUNDS

[75] Inventor: Kuo-Hua Chao, Houston, Tex.

[73] Assignee: Shell Oil Company, Houston, Tex.

[21] Appl. No.: 43,777

[22] Filed: Apr. 29, 1987

[51] Int. Cl.$^4$ .............................................. C07C 85/24
[52] U.S. Cl. ................................. 564/463; 564/467; 564/470
[58] Field of Search ........................ 564/463, 470, 469

[56] References Cited

FOREIGN PATENT DOCUMENTS 50-24203 3/1975 Japan ................................. 564/463

OTHER PUBLICATIONS

McGraw–Hill, Encyclopedia of Science & Technology 6th Ed. vol. 13, pp. 58–59 1987.

*Primary Examiner*—Howard T. Mars

[57] ABSTRACT

Alkylamines are self-alkylated to longer carbon chain alkylamines using a catalyst comprising a Group VIIB or a Group VIII metal supported on a porous inert carrier.

13 Claims, No Drawings

ALKYLATION OF AMINE COMPOUNDS

FIELD OF THE INVENTION

The present invention relates to the catalytic synthesis of longer chain alkylamines by the oligomerization or self-alkylation of mono-, di- and trialkylamines.

BACKGROUND OF THE INVENTION

The common method of alkylating organic compounds is by using alkylating agents such as olefins or alkylhalides in the presence of a Friedel Crafts catalyst. When amines are used as alkylating agents with Friedel Crafts catalysts, the alkylation reaction is severely inhibited by the fact that the amine poisons the catalyst by the formation of an acid-base compound.

U.S. Pat. No. 4,430,513, issued Feb. 7, 1984, discloses one method in which alkylamines can satisfactorily be used as alkylating agents. Specifically, this patent teaches the self-alkylation of alkylamine compounds which contain at least two alkyl substituents containing from about 2 to 6 carbon atoms. The alkylamine compounds are alkylated in the presence of homogeneous rhodium or cobalt carbonyls.

U.S. Pat. No. 4,562,291, issued December 31, 1985, discloses the self-alkylation of mono-, di- and trialkylamines using a homogeneous catalyst mixture comprising a tetra-fluoroborate salt and a ruthenium, an osmium or an iridium-containing compound.

In co-pending U.S. application Ser. No. 940,385 filed Dec. 10, 1986, is discussed the use of a homogeneous catalyst mixture comprising aluminum chloride in combination with cobalt and/or ruthenium carbonyl.

In co-pending U.S. Application Ser. No. 17,501 filed Feb. 24, 1987, is discussed the use of a homogeneous catalyst mixture comprising ruthenium carbonyl and a cyclopentadienyl metallocene.

The oligomerized alkylamines prepared by the process of the instant invention are useful for preparing detergent products and disinfectant products.

SUMMARY OF THE INVENTION

The present invention involves a process for the catalytic synthesis of long chain alkylamines. Specifically, mono-, di- or trialkylamines are oligomerized or self-alkylated to form longer chain alkylamines by contacting the mono-, di- and/or trialkylamines with a catalyst comprising a Group VIIB, a Group VIII metal, or mixtures thereof, supported on a porous inert support. Preferred catalysts comprise platinum supported on carbon granules. A particular advantage of the instant invention is that it can be used to convert alkylamines to their mono-alkylated amine products in high yield. Selectivities of the instant catalyst combinations result in the product amines being predominately (preferably greater than about a third, and more preferably greater than about a half) the mono-alkylates. This can result in simpler product mixes with concomitant lower separation costs.

DETAILED DESCRIPTION OF THE INVENTION

The present invention provides a process for synthesizing long chain alkylamines by self-alkylation or oligomerization of shorter chain alkylamines. Any typical alkylamine can be oligomerized in accordance with the present invention. The invention is particularly suitable for alkylating trialkylamines, particularly the $C_1$–$C_6$ alkyl amines, although the dialkylamines and monoalkylamines are also suitable. Oligomerization produces a mixture of various longer chain alkylamines. In a preferred embodiment, the instant process converts an amine predominately to its next higher alkylated homologues i.e., the mono-alkylated amines. For example, triethylamine is converted predominately to butyldiethylamine, butylethylamine, dibutylamine and dibutylethylamine. Thus, in a preferred embodiment amines of the general formula

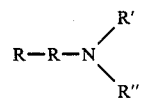

are prepared from amines of the general formula

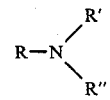

wherein R is alkyl, preferably $C_1$–$C_6$ alkyl and R' and R" are individually alkyl or hydrogen.

The reaction is run in the presence of a catalyst comprising a catalytically effective amount of a metal selected from Group VIIB and Group VIII of the Periodic Table (and mixtures of metals from Groups VIIB and VIII) supported on an inert support. The metals are preferably the "higher Group VIIB and Group VIII metals", that is rhenium and ruthenium, rhodium, palladium osmium, iridium and platinum. The more preferred metals are selected from the group consisting of platinum, palladium, rhodium, rhenium, ruthenium and mixtures thereof. The preferred catalytic metal is platinum.

The support used to prepare the catalysts used in the process of the instant invention are selected from the large number of conventional porous catalyst carriers or supports which are essentially inert under reaction conditions. The term "inert" being used herein to mean that the support does not adversely affect the oligomerization reaction. Such conventional materials are of natural or synthetic origin and preferably have a surface area greater than about 800 m²/g. Examples of supports believed to be suitable for preparing the instant catalysts are aluminas, silicas, aluminosilicates, zeolites, pumice, silicon carbide, clays, ceramics, carbon granules, charcoal, graphite and the like. Particularly preferred supports comprise carbon particles or granules. These carbon particles typically have sizes ranging from about 0.1 mm to about 5 mm and surface areas of greater than about 500 m²/g. Suitable carbon granules can be obtained commercially from Engelhard Corporation, Specialty Chemicals Division, Newark, N.J.

The amount of catalytically effective metal provided on the support will typically range from about 0.01 to about 25%w, although greater or lesser amounts can be used. Economics direct a preference to lesser amounts of metals. Preferred amounts range from about 0.1 to about 10% by weight of the total catalyst.

The catalyst are prepared in a conventional fashion, say, for example, by impregnation of the support with suitable solutions containing the dissolved catalytic metals (as ions or complexes) followed by drying and calcining. The catalysts are readily obtained from commercial sources as hydrogenation catalysts. Suppliers of these catalysts include Engelhard, Alfa, Baker and Strem. Engelhard supplies platinum on activated carbon granules which are particularly preferred for use in the instant process.

The reaction may be pressured with various neutral and reducing gases. Oxidizing gases such as air are to be avoided. Suitable pressurizing gases are nitrogen, carbon monoxide, hydrogen, syngas and the like.

The oligomerization is a liquid phase reaction. It is preferably carried out in the presence of a solvent, preferably an amine solvent. Most preferably the solvent is an aliphetic amine. Preferably the reactant amines are used as the reaction solvents. Other solvents such as alcohols, ethers, aromatics or paraffins can be used, but are less desirable.

The alkylation or oligomerization reaction conditions will vary considerably depending on the particular amine being alkylated. The higher molecular weight amines will require higher temperatures than the lower molecular weight amines. The optimum alkylation conditions can be determined by routine experimentation.

The oligomerization reaction is typically carried out at a temperature range of from about 50° C. to about 300° C., more preferably from about 150° C. to about 250° C., even more preferably from about 175° C. to about 250° C. Pressures will typically run from about 1 atmosphere to about 500 atmospheres, more preferably from about 1 to about 300 atmospheres and more preferably from about 20 to about 100 atmospheres. For flow conditions, liquid hourly space velocities (LHSV) will typically range from about 1 to about 10, although LHSV's outside this range can be utilized.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention may be accomplished in either a batch or continuous type operation. For example, when a batch type operation is to be employed, a quantity of the catalyst and amine compound along with an organic solvent, if one is to be used, will be placed in a pressure-resistant apparatus such as an autoclave of the stirring, mixing or rotating type. Following the addition of the catalyst and starting material, the apparatus is sealed, flushed with an inert gas such as nitrogen, and pressurized to the desired operating pressure with carbon monoxide and optionally hydrogen. Upon reaching the desired operating pressure, the apparatus is then heated to a predetermined operating temperature and maintained thereat for the desired residence time which may range from about 0.5 up to about 20 hours or more in duration. Upon completion of the desired residence time, heating is discontinued and after the apparatus and contents thereof have returned to room temperature, the excess pressure is discharged, the apparatus is opened, and the reaction mixture is recovered therefrom. After separation of the product mix from the catalyst, the former may then be subjected to conventional means of separating the components of said mix, said means including fractional distillation, fractional crystallization, etc.

It is also contemplated within the scope of this invention that the alkylation of the alkylamine compound may be accomplished in a continuous manner of operation. Such continuous operation typically uses a packed bed containing catalyst particles or a fluidized bed of catalyst particles. Packed beds or columns are preferred. When such a type of operation is employed, the starting material comprising the alkylamine is continuously charged to a bed or column packed with the catalyst particles which is maintained at the proper operating conditions of temperature and pressure. In addition any solvent is also continuously charged to the reaction apparatus either through separate lines or, if so desired, the components of the reaction mixture and any solvent may be admixed prior to entry into the reaction apparatus and the resulting mixture charged thereto in a single stream. After passage through the apparatus for a predetermined period of time, the reactor effluent is continuously withdrawn and subjected to conventional means of separation whereby the product mix is separated from any unreacted starting material or solvent which can then be recycled to the reaction apparatus to form a portion of the feedstock, while the product mix is subjected to further distillation to recover the various components of said mix.

The process of this invention is further described by the following illustrative embodiments which are provided for illustration and are not to be construed as limiting the invention.

Batch Reactions

EXAMPLE 1

To a 100 cc stainless steel screw top autoclave was added 40 ml of triethylamine and 1.80 gram of 2% platinum on carbon granules to provide 0.183 mmol of platinum. The catalyst was obtained from Engelhard Corporation (Catalog No. 1133201). The autoclave was sealed under inert atmosphere and flushed with carbon monoxide, following which the autoclave was pressurized to 100 psi with carbon monoxide. Thereafter, the autoclave was heated to a temperature of 220° C. and maintained there for a period of 19 hours. At the end of this period, heating was discontinued and the autoclave was allowed to return to room temperature. The excess pressure was discharged, the autoclave was opened, and the reaction product was recovered. The product was analyzed by means of gas liquid chromatography and mass spectroscopy. This analysis determined that there had been 89%w conversion of the triethylamine and that the triethylamine which had been converted to higher alkylamines (50%) was converted with the selectivity shown in Table I below.

TABLE 1

| Alklated Product | Weight Percent |
| --- | --- |
| butylethylamine | 36.0 |
| butyldiethylamine | 25.0 |
| dibutylamine | 16.0 |
| dibutylethylamine | 13.0 |
| hexyldiethylamine | 3.6 |
| tributylamine | 2.6 |

EXAMPLE 2

Example 1 was repeated using 120 ml of triethylamine and 15389 mg of 5% palladium on carbon (0.183 mmol of pd). This catalyst was obtained from Strem (Catalog No. 48-189). Analysis determined that there had been a 23%w conversion of the triethylamine and that the triethylamine which had been converted to higher alkylamines (50%) was converted with the selectivity shown in Table 2 below:

TABLE 2

| Alkylated Product | Weight Percent |
|---|---|
| butylethylamine | 7.0 |
| butyldiethylamine | 65.0 |
| dibutylethylamine | 2.0 |
| hexyldiethylamine | 16.0 |
| octyldiethylamine | 4.0 |
| decyldiethylamine | 1.0 |

EXAMPLE 3

Example 1 was repeated using 0.357 g of 10% platinum on alumina (0.183 mmol of pt). This catalyst was obtained from Engelhard (Catalog No. 1223404). Analysis determined that there had been a 1%w conversion of the triethylamine and that the triethylamine which had been converted to higher alkylamines (50%) was converted with a selectivity to butyldiethylamine of 90%w.

EXAMPLE 4

Example 1 was repeated using 1.50 g of 1.2% platinum on graphamet (0.092 mmol of pt). This catalyst was obtained from Alfa (Catalog No. 89125). Analysis determined that there had been a 1.0%w conversion of the triethylene amine and that the triethylamine which had been converted to higher alkylamines (50%) was converted with a selectivity to butyldiethylamine of 90.0%w.

EXAMPLE 5

Example 1 was repeated using 0.341 g of 10% rhenium on carbon 0.183 mmol of Re). This catalyst was obtained from Strem (Catalog No. 75-220). Analysis determined that there had been a 16%w conversion of the triethylamine and that the triethylamine which had been converted to higher alkylamines (50%) was converted with the selectivity shown in Table 3 below.

TABLE 3

| Alkylated Product | Weight Percent |
|---|---|
| butylethylamine | 6.0 |
| butyldiethylamine | 53.0 |
| dibutylethylamine | 2.0 |
| hexyldiethylamine | 9.0 |
| octyldiethylamine | 2.0 |

EXAMPLE 6

Example 1 was repeated using 120 ml of triethylamine and 0.389 g of 5% rhodium on carbon (0.183 mmol of Rh). This catalyst was obtained from Baker (Catalog No. 13-1833). Analysis determined that there had been a 13%w conversion of the triethylamine and that the triethylamine which had been converted to higher alkylamines (50%) was converted with the selectivity shown in Table 4 below:

TABLE 4

| Alkylated Product | Weight Percent |
|---|---|
| butylethylamine | 4.0 |
| butyldiethylamine | 74.0 |
| hexyldiethylamine | 14.0 |

TABLE 4-continued

| Alkylated Product | Weight Percent |
|---|---|
| octyldiethylamine | 4.0 |

EXAMPLE 7

Example 1 was repeated using 1.83 g of 2% ruthenium on graphite (0.36 mmol of ru). This catalyst was obtained from Alfa (Catalog No. 89127). Analysis determined that there had been a 0.6%w conversion of the triethylamine and that the triethylamine which had been converted (50%) was converted with a selectivity to butyldiethylamine of 90.0%w.

Comparative Example A

Example 1 was repeated using 0.0357 g of platinum black (unsupported, 0.183 mmol of pt). Analysis determined that there had been no conversion of the triethylamine.

Flow Reactions

EXAMPLE 8

15 Cubic centimeters of the 2% platinum catalyst used in Example 1 was loaded into a ¾ inch I.D. stainless steel reaction. The reactor was heated to 207° C. under one atmosphere of nitrogen pressure. 15 Cubic centimeters per hour of triethylamine was feed to the reaction. Analysis of the liquid product (by GLC and MS) determined that there had been a 68%w conversion of the triethylamine and that the triethylamine which had been converted to higher alkylamines (50%) was converted with the selectivity shown in Table 6 below:

TABLE 6

| Alklated Product | Weight Percent |
|---|---|
| butylethylamine | 37.0 |
| butyldiethylamine | 32.0 |
| dibutylamine | 12.0 |
| dibutylethylamine | 7.4 |
| hexyldiethylamie | 5.8 |

EXAMPLE 9

Example 8 was repeated using a triethylamine flow rate of 40 cc/hour. analysis determined that there had been a 34%w conversion of the triethylamine and that the triethylamine which had been coverted to higher alkylamines (50%) was converted with the selectivity shown in Table 7 below:

TABLE 7

| Alkylated Product | Weight Percent |
|---|---|
| butylethylamine | 20.0 |
| butyldiethylamine | 52.0 |
| dibutylamine | 5.1 |
| dibutylethylamine | 7.9 |
| hexyldiethylamine | 8.9 |

EXAMPLE 10

Example 8 was repeated using 15 cc/hour of diethylamine. Analysis determined that there has been a 44%w conversion of diethylamine and that the diethylamine which had been converted to higher alkylamines (50%) was converted with the selectivity shown in Table 8 below:

TABLE 8

| Alkylated Product | Weight Percent |
| --- | --- |
| butylethylamine | 58.0 |
| butyldiethylamine | 21.0 |
| dibutylamine | 11.7 |
| dibutlethylamine | 3.5 |
| hexyldiethylamine | 2.9 |
| tributylamine | 8.5 |
| octyldiethylamine | 2.1 |

EXAMPLE 11

Example 10 was repeated using 40 cc/hour of diethylamine. Analysis determined that there had been a 30%w conversion of diethylamine and that the diethylamine which had been converted to higher alkylamines (50%) was converted with the selectivity shown in Table 9 below:

TABLE 9

| Alklated Product | Weight Percent |
| --- | --- |
| butylethylamine | 55.0 |
| butyldiethylamine | 30.0 |
| dibutylamine | 7.9 |
| dibutylethylamine | 2.4 |
| hexyldiethylamine | 3.7 |

I claim:

1. A process for the liquid phase oligomerization of trialkylamines to produce longer carbon chain trialkylamines which process comprises contacting said, trialkylamines at oligomerization reaction conditions with a catalyst comprising a catalytically effective amount of one or more Group VIIB and a Group VIII metals supported on a porous inert support.

2. The process of claim 1 wherein the catalytic metals are selected from the group consisting of Ru, Rh, Pd, Re, Os, Ir, Pt and mixtures thereof.

3. The process of claim 2 wherein the catalytic metal is platinum.

4. The process of claim 2 wherein the support is carbon.

5. The process of claim 3 wherein the support is carbon.

6. The process of any one of claims 1-5 wherein the alkylamine is a $C_1$-$C_6$ trialkylamine.

7. The process of any one of claims 1-5 wherein the trialkylamine is selected from triethylamine, tributylamine and trihexylamine.

8. The process of any one of claims 1-5 wherein the amount of catalytic metal or the support ranges from about 0.01 to about 25% by weight at the total catalyst.

9. The process of any one of claims 1-5 wherein the amount of catalytic metal on the support ranges from about 0.1 to about 10 percent by weight of the total catalyst.

10. The process of any one of claims 1-5 wherein the temperature is maintained between about 50° C. and about 300° C.

11. The process of any one of claims 1-5 wherein the temperature is between about 150° C. and about 250° C.

12. The process of any one of claims 1-5 or any of claims 10-11 wherein the pressure is maintained between about 1 and about 500 atmospheres.

13. A process for preparing an amine of the general formula

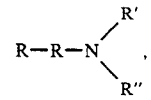

wherein R is $C_1$-$C_6$ alkyl and R' and R'' are $C_1$-$C_6$ alkyl, which process comprises oligomerizing an amine of the general

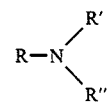

wherein R and R' are as defined above by contacting in the liquid phase said

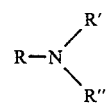

at a temperature of from about 175° C. to about 250° C. with a catalyst comprising about 0.1 to about 10 percent by weight of platinum on a carbon support.

* * * * *